United States Patent [19]

Rasmussen

[11] 4,437,737

[45] Mar. 20, 1984

[54] SCREEN AND METHOD OF EYE EXAMINATION USING SAME

[76] Inventor: Byron C. Rasmussen, 1035 N. Emporia, Wichita, Kans. 67214

[21] Appl. No.: 242,666

[22] Filed: Mar. 11, 1981

[51] Int. Cl.$^3$ .............................................. A61B 3/02
[52] U.S. Cl. .................................................. 351/237
[58] Field of Search .................... 351/36, 37, 38, 158, 351/23, 24, 30, 31; 350/125

[56] References Cited

U.S. PATENT DOCUMENTS

| | | | |
|---|---|---|---|
| 2,872,843 | 2/1959 | Kono | 351/230 |
| 3,025,755 | 3/1962 | Koetting | 351/23 |
| 3,037,424 | 6/1962 | Capetta | 350/125 |
| 3,300,269 | 1/1967 | Schultz | 351/24 |
| 3,969,020 | 7/1976 | Lynn et al. | 351/237 X |

Primary Examiner—John K. Corbin
Assistant Examiner—Rodney Bovernick
Attorney, Agent, or Firm—John H. Widdowson

[57] ABSTRACT

A method for examining the eyes of a patient. A screen for having light and indicia projected thereon from a light and indicia source in the examination of the eyes of a patient having a refraction apparatus over the eyes as in the nature of eyeglasses on the patient. The screen includes a frame, and a screen mounted on the frame. The combined frame-screen is parabolic. A mount attaches to the frame and is capable of permitting positioning the combined frame-screen about both a vertical and a horizontal axis to direct light therefrom. The method comprises positioning the eyes of the patient and the refraction apparatus at a distance from the parabolic screen approximately equal to the radius of the parabolic screen; situating the light and indicia source in front of the screen; projecting light and indicia from the light and indicia source on the screen; and adjusting the combined parabolic screen-frame about both the vertical and horizontal axis to optimumly direct light therefrom through the refraction apparatus.

6 Claims, 9 Drawing Figures

SCREEN AND METHOD OF EYE EXAMINATION USING SAME

BACKGROUND OF THE INVENTION

1. Field of the Invention

This invention provides for a screen and a method of eye examination using same.

2. Description of the Prior Art

U.S. Pat. No. 3,213,925 by Albee, Jr. discloses a screen mounted on a vertical surface for reception of the projected image and the screen may be adjusted to the desired degree. U.S. Pat. No. 3,263,561 by Jackson discloses a curved screen which is of high light reflecting characteristics. U.S. Pat. No. 970,913 by Ganzini teaches a curved screen structure. U.S. Pat. No. 2,820,393 by Wichers discloses a curved or parabolic screen which receives projected lights or spots for testing visual fields during an eye examination. None of the foregoing prior art teaches or suggests the particular screen and method of eye examination using same of this invention.

SUMMARY OF THE INVENTION

This invention accomplishes its desired objects by providing a screen apparatus for having light and indicia projected thereon from a light and indicia source in the examination of the eyes of a patient having a refraction apparatus mounted over the eyes as in the nature of eyeglasses on the patient. The screen apparatus comprises a frame, and a screen mounted on the frame. The combined frame-screen has a structure generally defining a parabola with respect to a horizontal cross section and essentially includes a radius approximately equal to the distance the eyes of the patient are from the combined screen-frame. A mounting means attaches to the frame and is capable of permitting positioning the combined frame-screen about both a vertical and a horizontal axis to direct light therefrom, and, in examining the eyes of the patient, to direct light to the eyes of the patient through the refraction apparatus. This invention also accomplishes its desired objects by providing a method for examining the eyes of a patient comprising the steps of: (a) positioning the eyes of a patient and the refraction apparatus at a distance from the parabolic screen approximately equal to the radius of the parabolic screen; (b) situating a light and indicia source in front of the screen means; (c) projecting light and indicia from the light and indicia source on the screen in order to direct light to the eyes of the patient through the refraction apparatus mounted over the eyes of the patient as in the nature of eyeglasses on the patient; and (d) adjusting the combined parabolic screen-frame about both the vertical and horizontal axis to optimumly direct light therefrom through the refraction apparatus.

It is an object of the invention to provide an eye chart and a method of eye examination using the same.

It is another object of the present invention to provide a brighter and easier discernible eye chart with less image distortion and better contrast of letters against a whiter background.

Still further objects of the invention reside in the provision of the eye chart screen to concentrate light directed to the patient by a projector, and to reflect the light to the patient.

These together with the various ancillary objects and features will become apparent as the following description proceeds are attained by this invention, a preferred embodiment being shown in the accompanying drawings, by way of example only, wherein:

DETAILED DESCRIPTION OF THE INVENTION

Figure 1:
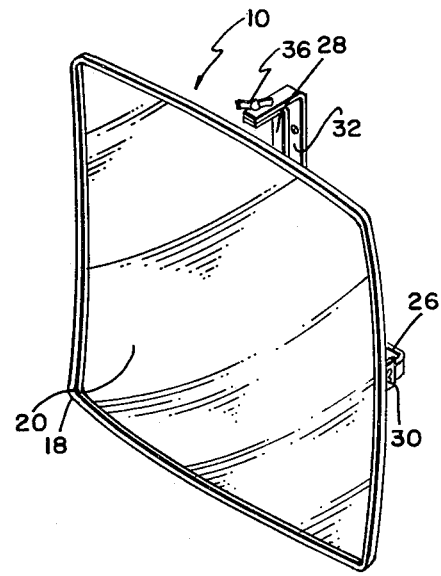
FIG. 1 is a perspective view of the parabolic screen.
Figure 2:
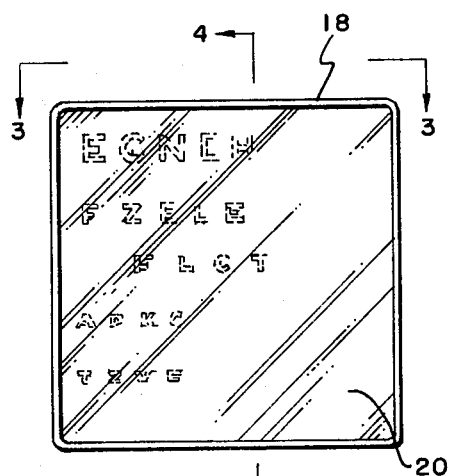
FIG. 2 is a front elevational view of the screen.
Figure 3:
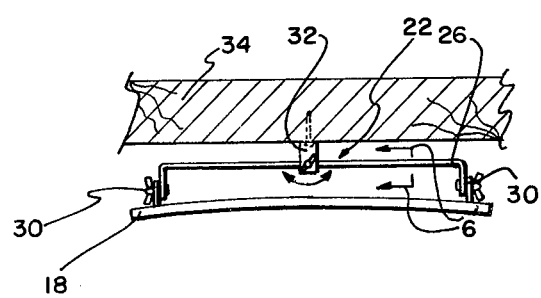
FIG. 3 is a top plan view taken in direction of the arrows and along the plane of line 4—4 in FIG. 2.

Referring in detail now to the drawings, wherein similar parts of the invention are identified by like reference numerals, there is seen a screen apparatus, generally illustrated as 10, for having light and indicia (as illustrated in FIG. 2) projected thereon from a light and indicia source 12 in the examination of the visual acuity of a patient 14 having a refraction apparatus 16 mounted over the eyes (see FIG. 5) as in the nature of eyeglasses on the patient 14. Screen apparatus 10 includes a frame 18 and a silver screen 20 mounted on the frame 18. The frame 18-screen 20 combination has a parabolic structure with respect to a cross section and has a radius approximately equal to the distance the eyes of the patient 14 are from the combined frame 18-screen 20. In a preferred embodiment of the invention, the distance the eyes of the patient 14 are from the combined frame 18-screen 20 and the radius are between about 5 and 25 feet; more preferably, the distance and the radius are 10 or 20 feet. Also, in a preferred embodiment of the invention, the distance of the light and indicia source 12 from the combined frame 18-screen 20 is also approximately equal to the distance the eyes of the patient 14 are from the same (see FIG. 5).

Figure 4:
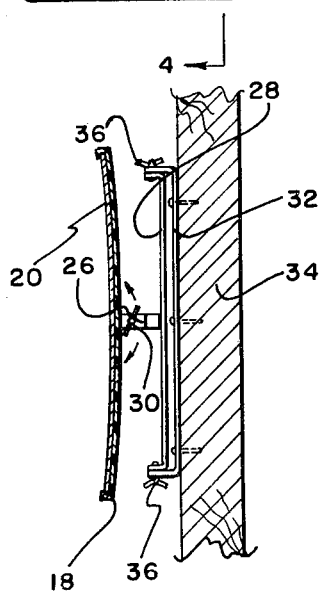
FIG. 4 is a vertical sectional view taken in direction of the arrows and along the plane of line 4—4 in FIG. 2.
Figure 8:
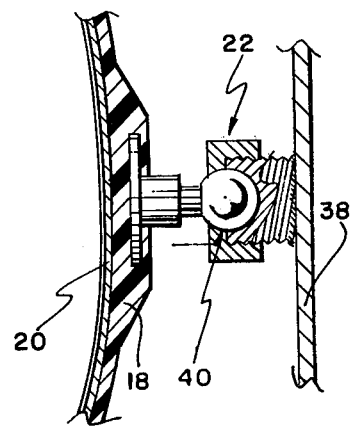
FIG. 8 is an enlarged sectional view of the swivel.
Figure 9:
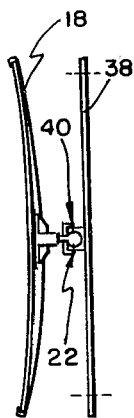
FIG. 9 is a side elevational view of the screen disclosing the swivel mounted on a bracket.
Figure 7:
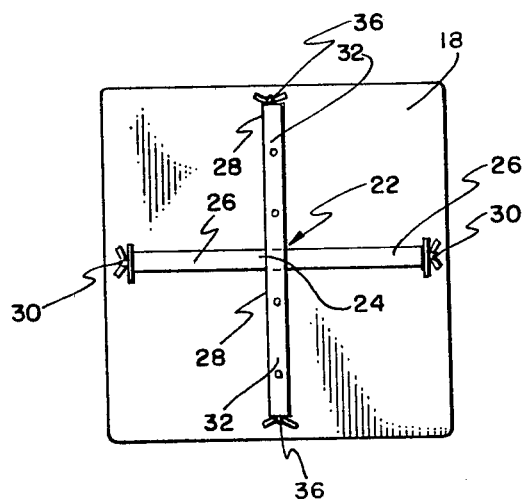
FIG. 7 is a back elevational view of the screen.

A mounting means, generally illustrated as 22, is attached to the frame 18 and has two embodiments which permit the positioning of the combined frame 18-screen 20 about both a vertical and a horizontal axis to optimumly direct light to the eyes of the patient 14 through the refraction apparatus 16. One embodiment (see FIGS. 3, 4, 6 and 7) having a horizontal arm 26 connected to a vertical arm 28. The horizontal arm 26 pivotally attaches to the frame 18 at 30 such as to enable horizontal pivotation (direction of the arrow in FIG. 4) of the combined frame 18-screen 20 about the horizontal axis. A bracket member 32 mounted to stationary object 34 is pivotally attached to the vertical arm 28 at 36—36 allowing vertical pivotation of the combined frame 18-screen 20 about the pivotation connecting points 36—36 of the vertical arm 28 and the bracket member 32. In the other embodiment of the mounting means 22 (see FIGS. 8 and 9), a mounting member 38 is mounted to the stationary object 34 and a swivel means, generally illustrated as 40, interconnects the frame 18 with the mounting member 38.

Figure 5:
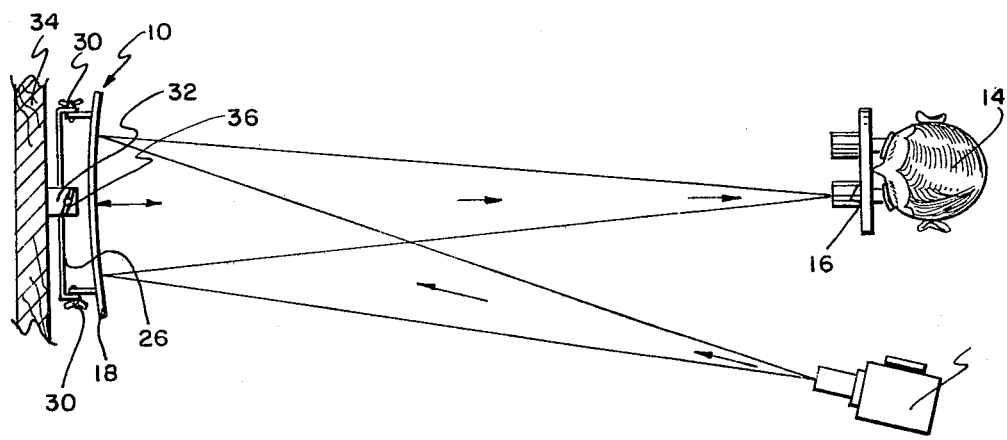
FIG. 5 is a top plan view of the light and indicia source projecting light onto the screen which reflects the same back through the refraction apparatus over the eyes of a patient.
Figure 6:
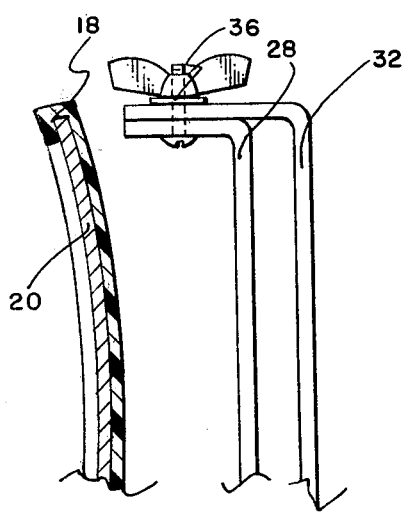
FIG. 6 is a vertical sectional view taken in direction of the arrows and along the plane of line 6—6 in FIG. 3.

With continuing reference to the drawings for operation of the invention and the method for examining the visual acuity of the patient 14, the patient 14, having the refraction apparatus 12 mounted over the eyes as in the nature of eyeglasses on the patient 14, is positioned at a distance (which is preferably 10 or 20 feet) from the combined parabolic frame 18-screen 20 approximately equal to the radius (10 or 20 feet) of the parabolic frame 18-screen 20. The light and indicia source 12 is situated in front of the frame 18-screen 20, preferably at the same distance (10 or 20 feet) from the frame 18-screen 20 that the eyes of the patient 14 are located from the frame 18-screen 20. Light and indicia, such as that illustrated in FIG. 2, is projected on the screen 20 in order to direct the same (as illustrated in FIG. 5) to the eyes of the patient 14 through the refraction apparatus 16. The mounting means 22, either the embodiment in FIGS. 8-9 or the embodiment in FIGS. 3-7, is subsequently utilized to adjust the combined frame 18-screen 20 about both the vertical and horizontal axis to optimumly direct light from the screen 20 through the refraction apparatus 16, as illustrated in FIG. 5.

Thus, by the practice of this invention, there is provided a screen means 10 which can be adjusted to provide optimum adjustment of the combined frame 18-screen 20 for correct alignment relative to the light and indicia source 12 and patient 14. Eye refraction can be done in daylight which is the normal way of seeing Any patient 14 being refracted can have a higher threshold of evaluating small differences of lens power thereby producing a more accurate eye refraction. Because of the clearness and sharpness of the indicia, patient 14 can make decisions faster and more accurately.

While the present invention has been described with references to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. A screen apparatus for having light and more contrasting, brighter and clearer indicia reflected from the screen from a light and indicia source in the examination of the direct visual acuity of a patient having a refraction apparatus mounted over the eyes as in the nature of eyeglasses on the patient comprising a frame; a screen constructed and adapted to reflect light mounted on said frame, said combined frame-screen having a structure generally defining a parabola with respect to a cross section and essentially including a radius approximately equal to the distance the eyes of the patient are from the combined screen-frame; and a mounting means attached to said frame and capable of permitting positioning of the combined frame-screen about both a vertical and a horizontal axis to direct light to the eyes of the patient through the refraction apparatus, said mounting means comprises a cross member having a horizontal arm connected to a vertical arm said horizontal arm pivotally attaching to the frame such as to enable horizontal pivotation of the combined screen-frame member about the horizontal axis; a bracket member mounted to a stationary object and pivotally attached to the vertical arm allowing vertical pivotation of the combined screen-frame about the pivotation connecting points of the vertical arm and the bracket member, said distance of the eyes of the patient and said radius are between about 5 and 25 feet, and said distance of said light and indicia source from the screen is approximately equal to the distance the eyes of the patient are from the screen.

2. A method for examining the direct visual acuity of a patient comprising the steps of:
 (a) positioning the eyes of a patient, having a refraction apparatus mounted over the eyes as in the nature of eyeglasses on the patient, at a distance from and in front of a parabolic screen means constructed and adapted to reflect light approximately equal to the radius of the parabolic screen means;
 (b) situating a light and indicia source at a distance in front of the parabolic screen means approximately equal to the distance that the eyes of the patient are from the screen;
 (c) projecting light and indicia from the light and indicia source onto the screen in order to direct light to the eyes of the patient through the refraction apparatus; and
 (d) adjusting the parabolic screen means about both the vertical and horizontal axis to optimumly direct light therefrom through the refraction apparatus.

3. The method of claim 3 wherein said screen means comprises a frame; a screen mounted on said frame, said combined frame-screen having a structure generally defining the said parabolic shape with respect to a cross section and essentially includes said radius approximately equal to the distance the eyes of the patient are from the combined screen-frame; and a mounting means attached to said frame and capable of permitting positioning of the combined frame-screen about both the vertical and horizontal axis.

4. The method of claim 3 wherein said mounting means comprises a cross member having a horizontal arm connected to a vertical arm, said horizontal arm pivotally attaching to the frame such as to enable horizontal pivotation of the combined screen-frame member about the horizontal axis; a bracket member mounted to a stationary object and pivotally attached to the vertical arm allowing vertical pivotation of the combined screen-frame about the pivotation connecting points of the vertical arm and the bracket member.

5. The method of claim 3 wherein said mounting means comprises a mounting member mounted to a stationary object and a swivel means interconnecting the frame with the mounting member.

6. A screen apparatus for having light and more contrasting, brighter and clearer indicia reflected from the screen from a light and indicia source in the examination of the direct visual acuity of a patient having a refraction apparatus mounted over the eyes as in the nature of eyeglasses on the patient comprising a frame; a screen constructed and adapted to reflect light mounted on said frame, said combined frame-screen having a structure generally defining a parabola with respect to a cross section and essentially including a radius approximately equal to the distance the eyes of the patient are from the combined screen-frame; and a mounting means attached to said frame and capable of permitting positioning of the combined frame-screen about both a vertical and a horizontal axis to direct light to the eyes of the patient through the refraction apparatus, said mounting means comprises a mounting member mounted to a stationary object and a swivel means interconnecting the frame with the mounting member, said distance of the eyes of the patient and the radius are between about 5 and 25 feet, and said distance of said light and indicia source from the screen is approximately equal to the distance the eyes of the patient are from the screen.

* * * * *